United States Patent [19]

Hibst et al.

[11] Patent Number: 5,306,144

[45] Date of Patent: Apr. 26, 1994

[54] DEVICE FOR DETECTING DENTAL CARIES

[75] Inventors: Raimund Hibst, Erbach; Karsten Konig, Blaustein, both of Fed. Rep. of Germany

[73] Assignee: Kaltenbach & Voigt GmbH & Co., Fed. Rep. of Germany

[21] Appl. No.: 3,267

[22] Filed: Jan. 12, 1993

[30] Foreign Application Priority Data

Jan. 14, 1992 [DE] Fed. Rep. of Germany ....... 4200741

[51] Int. Cl.$^5$ .......................... A61C 1/00; A61C 3/00; A61B 6/00; G01J 3/30
[52] U.S. Cl. ...................................... 433/29; 128/665; 356/317; 356/341
[58] Field of Search .................. 433/29, 215, 229; 128/777, 665, 634; 356/317, 318, 341

[56] References Cited

U.S. PATENT DOCUMENTS

| | | | |
|---|---|---|---|
| 3,136,310 | 6/1964 | Meltzer | 128/634 |
| 4,479,499 | 10/1984 | Alfano | 356/317 |
| 5,003,977 | 4/1991 | Suzuki et al. | 128/634 |

*Primary Examiner*—Gene Mancene
*Assistant Examiner*—Cindy A. Cherichetti
*Attorney, Agent, or Firm*—Scully, Scott, Murphy & Presser

[57] ABSTRACT

A device for detecting dental caries has an illumination device which emits radiation of a pre-determined wavelength towards a tooth. A filter accepts radiation returned by the tooth in a pre-determined spectral range. The accepted radiation is evaluated for caries detection. The illumination device has at least one light guide, by means of which the radiation can be supplied to the tooth. The illumination device emits radiation in the spectral range from 360 to 580 nm. The filter accepts the returned radiation in the spectral range above 620 nm. The device can be used in a flexible manner and enables a low level of caries to be identified.

39 Claims, 3 Drawing Sheets

DEVICE FOR DETECTING DENTAL CARIES

TECHNICAL FIELD OF THE INVENTION

The invention concerns a device for detecting dental caries, having an illumination device which emits radiation of a pre-determined wavelength towards at least one tooth, and having at least one filter which accepts radiation returned by the tooth in a pre-determined spectral range, with the accepted radiation being evaluated for the detection of caries.

BACKGROUND OF THE INVENTION AND PRIOR ART

A device of this type is described in the journal SPIE, Vol. 907, Laser Surgery: Characterization and Therapeutics, 1988, S. Albin et al., "Laser Induced Fluorescence of Dental Caries", pages 96 to 98. In the known device, a laser emits monochromatic radiation towards the tooth, and this induces fluorescent radiation. From carious places of the tooth there is issued fluorescent radiation which is characteristic of caries and differs from the returned radiation of a healthy tooth in its intensity and spectral distribution. The returned radiation is observed using a filter. The places of the tooth affected by caries appear as dark spots during observation.

The known device is provided for laboratory operation, in which optimum test conditions are present and usable test results, even in the case of low sensitivity of the device, can be achieved. For practical use in dental diagnosis, however, it is necessary to increase the sensitivity of the device considerably in order to detect caries. Furthermore, the known device is difficult to handle, so that it is not suitable as a means of diagnosis for use with humans or animals.

OBJECT OF THE INVENTION

It is an object of the invention to indicate a device for detecting dental caries, which device can be used in a flexible manner and can identify a low level of caries.

SUMMARY OF THE INVENTION

According to the present invention there is provided a device for detecting dental caries, having an illumination device which emits radiation of a pre-determined wavelength towards at least one tooth, and having at least one filter which accepts radiation returned by the tooth in a pre-determined spectral range, the accepted radiation being evaluated for caries detection, wherein the illumination device has at least one light guide, by means of which the radiation can be supplied to the tooth, in that the illumination device emits radiation in the spectral range from 360 to 580 nm, and in that the filter accepts returned radiation in the spectral range above 620 nm.

In the invention, radiation is supplied by way of a light guide to the tooth to be examined. Such a light guide can be rigid or flexible, it can be equipped at its end facing towards the tooth with optical means for directed beam guidance, and/or its dimensions can be adapted to the region of the patient's mouth and to the tooth. Exchangeable attachments, for example tilted mirrors or lenses, which make examination of the tooth easier, can be attached in a known manner to the light guide. Use of the light guide thus makes it easier to supply radiation in a directed manner to the regions of the tooth or teeth to be examined. The device according to the invention can therefore be adapted in a flexible manner to different requirements in everyday practice for detecting dental caries in animals and humans.

Furthermore, in the invention the spectral range of the radiation accepted by the filter is restricted at the lower end. This means that mainly the fluorescent radiation is filtered out and the interfering background radiation with short wavelengths is masked. The carious places of the tooth are thus displayed as bright spots which stand out clearly against the background. A condition of carious disease can thus be detected with a high level of accuracy and reliability. The device according to the invention is therefore very suitable for the early diagnosis of caries.

In practical tests it has been shown that caries pathogens react sensitively during irradiation with light in the spectral range indicated, and die out with a sufficiently strong intensity of radiation. With the device according to the invention, it is therefore possible to carry out dental caries treatment with simultaneous observation of the location of the treatment. This makes possible non-invasive, pain-free, selectively active, extremely gentle caries treatment which is particularly suitable for the treatment of caries in the early stage and for prophylaxis.

A preferred exemplary embodiment is characterized in that the filter accepts returned radiation in the spectral range from 620 to 720 nm. Within this spectral range the fluorescent spectrum emitted by dental caries has maximum points, that is to say, the yield of fluorescent radiation from converted excitation energy is high. The sensitivity of the device to caries is thereby further increased. Moreover, with this spectral range the distance from the spectral range of the excitation radiation in the spectral range from 360 to 580 nm is great, so that this excitation radiation is substantially suppressed and cannot distort the result. The carious places can therefore be detected with a high level of contrast.

A further exemplary embodiment is characterized in that the illumination device emits radiation in the spectral range from 360 to 420 nm.

In this spectral range, the intensity of returned radiation is particularly high, so that a very sensitive detection of carious places is possible. With a wavelength of supplied radiation in the region around 406 nm, sensitivity is at a maximum. Furthermore, with this spectral range the distance from the spectral range above 620 nm of the radiation emitted by the tooth is great, so that the supplied radiation is substantially suppressed and does not distort the result. In this way, the carious places of the tooth can be correctly detected.

A further exemplary embodiment is characterized in that the illumination device emits radiation in the spectral range from 470 to 580 nm.

With this spectral range, supplied radiation has a greater depth of penetration and can penetrate deep regions of the tooth, or pass through film on the teeth. It thus becomes possible to spot hidden disease centers. For irradiation there is preferably provided a radiation source which emits approximately monochromatic radiation with a wavelength around 470, 500, 540 or 580 nm.

For quantitative evaluation of returned radiation, in a further exemplary embodiment a detector is connected after the filter, seen in the direction of the returned radiation, which detector converts the radiation supplied to it into a first electrical signal. This signal, which can be indicated in a known manner, is approximately proportional to the radiation intensity detected by the detector. It can therefore be used in the quantitative assessment of the extent of the caries condition detected.

Practical tests have shown that the respective spectra of the radiation returned by healthy hard tooth substance and hard tooth substance altered by caries are significantly different. This effect is utilized in an exemplary embodiment. In this development there is provided a further filter which accepts the radiation returned by the tooth in a further spectral range which differs from the spectral range of acceptance of the first filter, whereby the detector or a further detector converts the filtered radiation into a second electrical signal, which is supplied to a quotient-forming element which forms a quotient from the first signal and the second signal, which quotient serves as a measure of the presence of caries.

During the testing of the invention, different behaviour of the radiation returned by a carious tooth and a healthy tooth has proved to show up particularly clearly when the intensity of the returned radiation in the spectral range from 620 to 720 nm is compared with that in the range from 540 to 560 nm. The spectral range from 620 to 720 nm comprises maximum intensities of fluorescent radiation caused by caries, while in the spectral range from 540 to 560 nm there is no conspicuous behaviour. The radiation intensity in the latter range can therefore be used as a reference. By means of the measures of this development, it is possible to give an objective judgement about the condition of disease.

A further advantage of the formation of a quotient is that the result is independent of the intensity of the supplied radiation. If the intensity of the supplied radiation changes, for example as a result of aging of the beam source or fluctuations in the power supply, then the quotient nevertheless remains constant with otherwise identical test conditions. Applicability of the invention in practice is therefore further improved.

BRIEF DESCRIPTION OF THE DRAWINGS

Exemplary embodiments of the invention are explained in the following with reference to the drawings.

DETAILED DESCRIPTION OF PREFERRED EMBODIMENTS ACCORDING TO THE INVENTION

Figure 1:
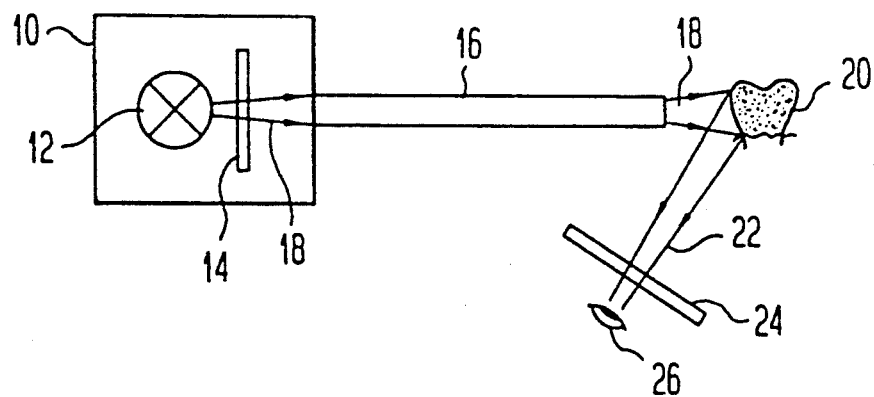
FIG. 1 shows a device for the visual diagnosis of dental caries.

In FIG. 1 is shown the basic construction of a device according to the invention for the detection and treatment, if required, of dental caries. An illumination device 10 has a beam source 12 which emits radiation in a spectral range from 360 to 420 nm. As the radiation source 12 there can be used a mercury-vapor lamp, a krypton laser, a halogen lamp or a dye laser. For filtering out the desired spectral range, a radiation filter 14 is arranged in front of the beam source 12.

The illumination device 10 is provided with a light guide 16 which directs radiation 18 emitted by the beam source 12 towards a tooth 20 to be examined. The radiation 22 radiated back by the surface of the tooth 20 as a result of reflection and fluorescence is filtered by a filter 24 which absorbs or reflects radiation having a wavelength of less than 620 nm and accepts radiation of a greater wavelength. The filter 24 is mounted on a spectacle frame (not shown) which is worn by a person for visual observation (indicated by an eye 26). The supplied radiation 18 induces in the regions of the tooth 20 affected by caries, a characteristic fluorescent radiation, the spectral fractions of which having wavelengths above the acceptance wavelength of the filter 24 reach the eye 26. Carious places of the tooth 20 can consequently be observed.

The device according to FIG. 1 can also be used in principle for caries therapy. For this purpose, a beam source 12 with higher radiation intensity must be used, for instance a laser. The caries pathogens react sensitively to the radiation with a wavelength in the range from 360 to 420 nm and die off. The location of the caries treatment can be observed through the filter 24.

Figure 2:
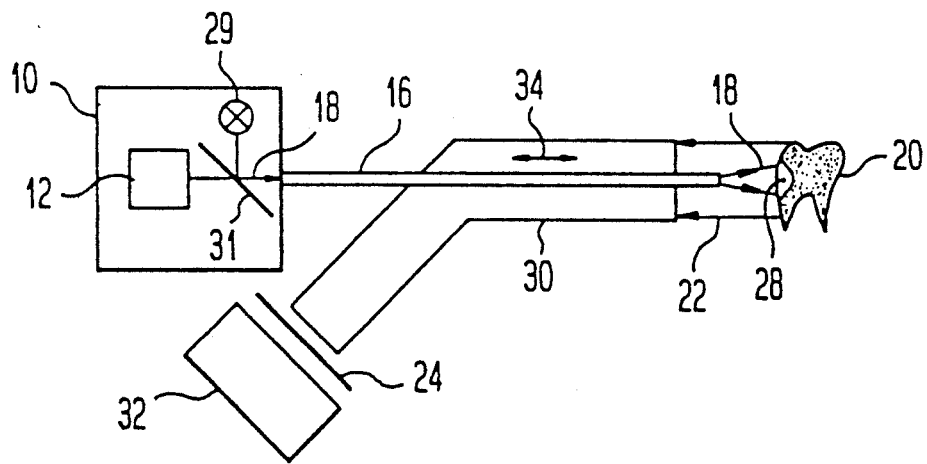
FIG. 2 shows another device in which the incident and returned fluorescent radiation is guided in light guides.

In the following Figures are shown further exemplary embodiments in which identical parts are respectively denoted in the same way. In FIG. 2 a laser is used as the beam source 12. Its monochromatic radiation 18 is supplied by way of the light guide 16 to the tooth 20. In addition, the illumination device 10 comprises a further light source 29 which generates white light of variable intensity which is added to the beam 18 by way of a separating mirror 31. The light guide 16 is surrounded by an outer light guide 30 having orderly fiber bundles which serve for image transmission. The light guide 16 is arranged displaceably with respect to the outer light guide 30, as is indicated by an arrow 34. In a withdrawn position in which the end of the light guide 16 facing the tooth 20 is near the end of the outer light guide 30, the radiation 18 illuminates a large surface of the tooth 20. In a position of the light guide 16 displaced further towards the tooth 20, individual places of the tooth 20 can be examined more closely. For example, it is possible to examine a cavity 28 in the tooth 20 more closely and to treat it if required.

The image-forming radiation 22 conveyed by the external light guide 30 is filtered by the filter 24 and supplied to a camera 32, by means of which there can be produced pictures of the tooth 20. The white light emitted by the further radiation source 29 serves to brighten the background, so that the contours of the tooth 20 can still be seen despite filtering through the filter 24, or when the filter 24 is pivoted outwards.

Figure 3:
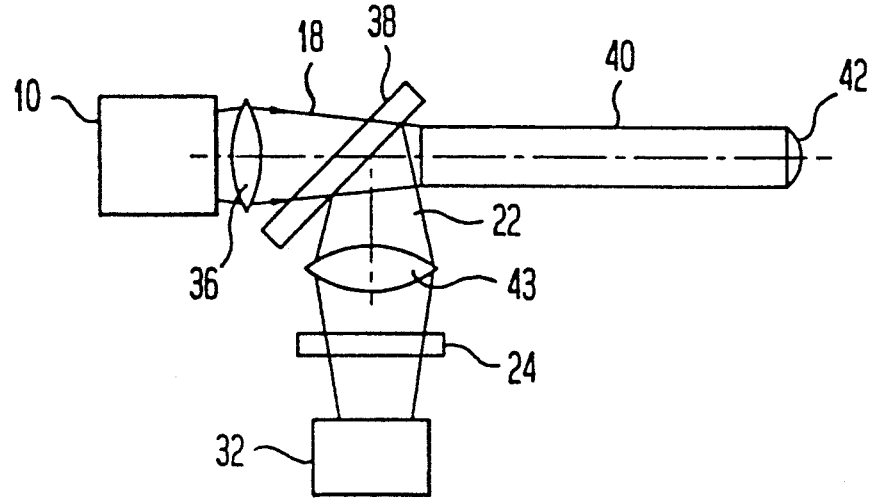
FIG. 3 shows a device having an image guide.

In FIG. 3, the radiation 18 emitted by the illumination device 10 is focused by means of a collector lens 36 and supplied to an image guide 40 by way of a partially transparent separating mirror 38. This image guide consists of a coherent or orderly fiber bundle in which the individual fibers of the input and output surface of the image guide 40 are arranged in the same way. The output surface of the image guide 40 is provided with a lens 42 which improves the image function of the image guide 40. The radiation 22 returned by a tooth (not shown) is also guided in the image guide 40 and reflected outwards at the separating mirror 38 towards a field lens 43, the filter 24 being connected after the separating mirror 38. The image conveyed by the image guide 40 can be recorded by the photographic or video camera 32. Instead of the camera 32 there can also be a detector device which forms an electrical signal from the radiation supplied to it. With the aid of this signal, it is possible to quantify the result of the examination of carious teeth.

Figure 4:
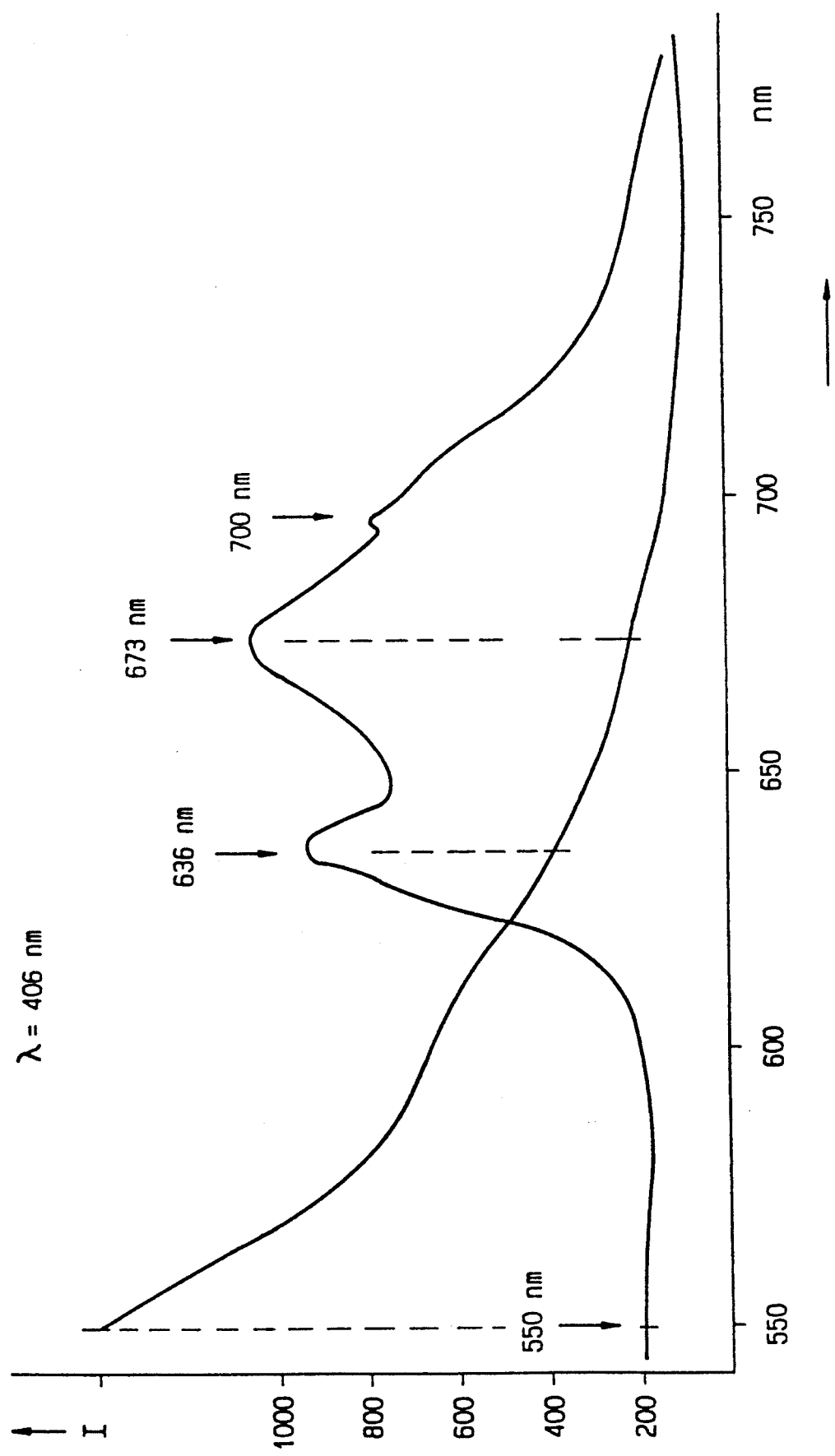
FIG. 4 shows curves of the radiation intensity of the returned radiation versus the wavelength, for a carious tooth and a healthy tooth.

In FIG. 4 there are plotted the curves of the radiation intensity I returned by a tooth in relative units versus the wavelength in nm, once for healthy enamel and a second time for carious enamel. The incident radiation, that is to say, the excitation radiation, has the wavelength 406 nm. As can be seen from the diagram, the curves shown differ from each other. In particular, the intensity curve for carious enamel shows three maximum intensities at 636, 673 and 700 nm. The difference in fluorescent behaviour of carious and healthy enamel is utilized in an exemplary embodiment of the invention, which is described in the following, for the qualitative and quantitative detection of caries.

Figure 5:
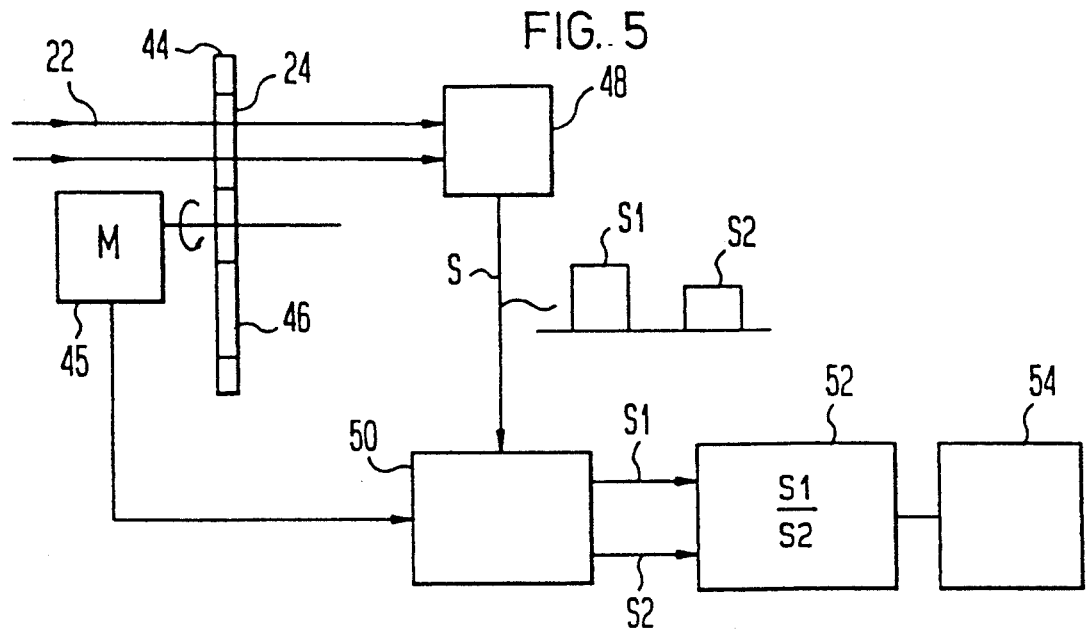
FIG. 5 shows a detector device in which a filter wheel is placed in the beam path.

In the detection device shown in FIG. 5, the filter 24 and a further filter 46 are arranged on a filter wheel 44. The filters 24, 46 are narrow band filters and accept wavelengths around 636 nm and 550 nm, respectively. When the filter wheel 44 is rotated by a motor 45, the filters 24, 46 are brought in turn into the beam path of the returned radiation 22. A photodiode 48 converts the filtered radiation supplied to it into an electrical signal S comprising the time-shifted partial signals S1 and S2, which are each proportional to a radiation intensity accepted by the filters 24 and 46, respectively. The signal S is supplied to a demultiplexer 50 which scans it synchronously with the rotation of the filter wheel 44 and separates the partial signals S1, S2 from the signal S. These partial signals S1, S2 are supplied to a quotient-forming element 52 which forms a quotient from them. The result is supplied to a decision module 54, where it is compared with characteristic reference values determined beforehand, for example from the diagram according to FIG. 4. In dependence upon the comparison it is then indicated whether the place of the tooth examined is affected by caries or not. The quotient itself serves as a criterion for the presence of caries.

Figure 6:
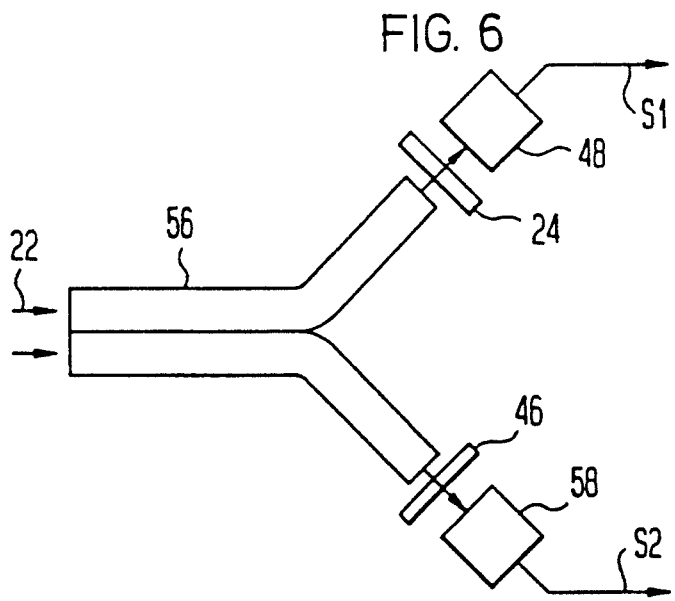
FIG. 6 shows a detector device with a divided light guide.

In FIG. 6, another detector device is shown in which the returned radiation 22 is guided in a light guide or a light guide bundle 56 which divides up the radiation 22. A first portion of this radiation 22 is supplied by way of the filter 24 to the detector 48, which generates the partial signal S1. The other portion of the radiation 22 is supplied by way of the filter 46 to a further detector 58, which generates the partial signal S2. The partial signals S1, S2 are then processed further as in the exemplary embodiment according to FIG. 5.

Figure 7:
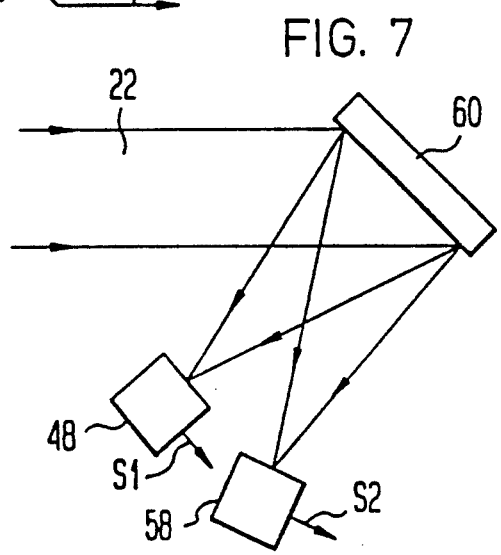
FIG. 7 shows a detector device for the spectrum analysis of the returned radiation by means of a reflection grating.

In FIG. 7, a reflection grating 60 is placed in the beam path of the returned radiation 22, which reflection grating reflects and focuses the radiation 22, in dependence upon the wavelength, in different directions. The detectors 48, 58 are arranged so that they detect the radiation 22 at the above-mentioned wavelengths and generate the partial signals S1 and S2.

What is claimed is:

1. Device for detecting dental caries, having an illumination device which emits radiation at a predetermined wavelength in the spectral range from 360 to 580 nm towards at least one tooth, and having at least one filter which accepts radiation returned by the tooth in a predetermined spectral range above 620 nm, the accepted radiation being evaluated for caries detection, wherein the illumination device has at least one light guide, by means of which the radiation is supplied to the tooth, and wherein a detector is connected after the filter, seen in the direction of the returned radiation, which detector converts the radiation supplied to it into a first electrical signal, and a further filter is provided which accepts radiation returned by the tooth in a further spectral range different from the spectral range of the filter, and the detector converts the filtered radiation into a second electrical signal which is supplied to a quotient-forming element, which forms a quotient from the first signal and the second signal, which quotient serves as a measure of the presence of caries.

2. Device according to claim 1, wherein the filter and the further filter are arranged on a chopper disc and can be placed in turn in the beam path of the returned radiation, in that the detector detects the filtered radiation, and in that the first signal and second signal are generated by means of scanning synchronous with the rotation of the chopper disc, from the signal delivered by the detector.

3. Device according to claim 1, wherein the returned radiation is detected by at least two light guide fibers which are respectively provided, at the end facing away from the tooth, with the filter and the further filter, respectively, and there being arranged after each filter a detector which detects the filtered radiation.

4. Device according to claim 1, wherein the filter accepts radiation of a wavelength in the region around 636 or 673 nm and the further filter accepts radiation of a wavelength in the region around 550 nm.

5. Device according to claim 1, wherein the filter accepts returned radiation in the spectral range from 620 to 720 nm.

6. Device according to claim 1, wherein the illumination device emits radiation in the spectral range from 360 to 420 nm.

7. Device according to claim 1, wherein the illumination device emits radiation in the spectral range from 470 to 580 nm.

8. Device according to claim 1, wherein the filter is arranged on a spectacle frame.

9. Device according to claim 1, wherein an image guide is provided as the light guide.

10. Device according to claim 1, wherein the light guide or light guides are accommodated by an endoscope, to which a camera can be attached.

11. Device according to claim 1, wherein the illumination device comprises a further light source which generates white light which can be added to the emitted radiation.

12. Device for detecting dental caries, having an illumination device which emits radiation at a predetermined wavelength in the spectral range from 360 nm to 580 nm towards at least one tooth, and having at least one filter which accepts radiation returned by the tooth in a predetermined spectral range above 620 nm, the accepted radiation being evaluated for caries detection, wherein the illumination device has at least one light guide, by means of which the radiation is supplied to the tooth, and wherein a detector is connected after the filter, seen in the direction of the returned radiation, which detector converts the radiation supplied to it into a first electrical signal, and a further filter is provided which accepts radiation returned by the tooth in a further spectral range different from the spectral range of the filter, and a further detector converts the filtered radiation into a second electrical signal which is supplied to a quotient-forming element, which forms a quotient from the first signal and the second signal, which quotient serves as a measure of the presence of caries.

13. Device according to claim 12, wherein the filter and the further filter are arranged on a chopper disc and can be placed in turn in the beam path of the returned radiation, in that the detector detects the filtered radiation, and in that the first signal and second signal are generated by means of scanning synchronous with the rotation of the chopper disc, from the signal delivered by the detector.

14. Device according to claim 12, wherein the returned radiation is detected by at least two light guide fibers which are respectively provided, at the end facing away from the tooth, with the filter and the further filter, respectively, and there being arranged after each filter a detector which detects the filtered radiation.

15. Device according to claim 12, wherein the filter accepts radiation of a wavelength in the region around 636 or 673 nm and the further filter accepts radiation of a wavelength in the region around 550 nm.

16. Device according to claim 12, wherein the filter accepts returned radiation in the spectral range from 620 to 720 nm.

17. Device according to claim 12, wherein the illumination device emits radiation in the spectral range from 360 to 420 nm.

18. Device according to claim 12, wherein the illumination device emits radiation in the spectral range from 470 to 580 nm.

19. Device according to claim 12, wherein the filter is arranged on a spectacle frame.

20. Device according to claim 12, wherein an image guide is provided as the light guide.

21. Device according to claim 12, wherein the light guide or light guides are accommodated by an endoscope, to which a camera can be attached.

22. Device according to claim 12, wherein the illumination device comprises a further light source which generates white light which can be added to the emitted radiation.

23. Device for detecting dental caries, having an illumination device which emits radiation at a predetermined wavelength in the spectral range from 360 to 580 nm towards at least one tooth, and having at least one filter which accepts radiation returned by the tooth in a predetermined spectral range above 620 nm, the accepted radiation being evaluated for caries detection, wherein the illumination device has at least one light guide, by means of which the radiation is supplied to the tooth, and wherein the at least one light guide is provided on the side of the illumination device with a separating mirror, the separating surface of which is inclined at an angle of substantially 45° from the optical axis of the light guide.

24. Device according to claim 23, wherein the filter accepts returned radiation in the spectral range from 620 to 720 nm.

25. Device according to claim 23, wherein the illumination device emits radiation in the spectral range from 360 to 420 nm.

26. Device according to claim 23, wherein the illumination device emits radiation in the spectral range from 470 to 580 nm.

27. Device according to claim 23, wherein the filter is arranged on a spectacle frame.

28. Device according to claim 23, wherein an image guide is provided as the light guide.

29. Device according to claim 23, wherein the light guide or light guides are accommodated by an endoscope, to which a camera can be attached.

30. Device according to claim 23, wherein the illumination device comprises a further light source which generates while light which can be added to the emitted radiation.

31. Device for detecting dental caries, having an illumination device which emits radiation at a predetermined wavelength in the spectral range from 360 to 580 nm towards at least one tooth, and having at least one filter which accepts radiation returned by the tooth in a predetermined spectral range above 620 nm, the accepted radiation being evaluated for caries detection, wherein the illumination device has at least one light guide, by means of which the radiation is supplied to the tooth, and wherein the light guide is surrounded by an outer light guide which guides the returned radiation.

32. Device according to claim 31, wherein the light guide is arranged displaceably within the outer light guide surrounding it.

33. Device according to claim 31, wherein the filter accepts returned radiation in the spectral range from 620 to 720 nm.

34. Device according to claim 31, wherein the illumination device emits radiation in the spectral range from 360 to 420 nm.

35. Device according to claim 31, wherein the illumination device emits radiation in the spectral range from 470 to 580 nm.

36. Device according to claim 31, wherein the filter is arranged on a spectacle frame.

37. Device according to claim 31, wherein an image guide is provided as the light guide.

38. Device according to claim 31, wherein the light guide or light guides are accommodated by an endoscope, to which a camera can be attached.

39. Device according to claim 31, wherein the illumination device comprises a further light source which generates white light which can be added to the emitted radiation.

* * * * *